US006855556B2

(12) United States Patent
Amiss et al.

(10) Patent No.: US 6,855,556 B2
(45) Date of Patent: Feb. 15, 2005

(54) BINDING PROTEIN AS BIOSENSORS

(75) Inventors: Terry J. Amiss, Cary, NC (US); Colleen M. Nycz, Raleigh, NC (US); J. Bruce Pitner, Durham, NC (US); Douglas B. Sherman, Durham, NC (US); David J. Wright, Chapel Hill, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/040,077

(22) Filed: Jan. 4, 2002

(65) Prior Publication Data

US 2003/0134346 A1 Jul. 17, 2003

(51) Int. Cl.$^7$ ................................................ G01N 33/48
(52) U.S. Cl. ........................ 436/95; 438/86; 438/164; 438/172; 435/7.2; 435/14; 435/287.1; 435/817
(58) Field of Search .............................. 436/56, 86, 95, 436/164, 172; 435/14, 287.1, 7.2, 817, 814

(56) References Cited

U.S. PATENT DOCUMENTS

| | | | |
|---|---|---|---|
| 4,703,756 | A | 11/1987 | Gough et al. |
| 4,704,029 | A | 11/1987 | Van Heuvelen |
| 5,001,054 | A | 3/1991 | Wagner |
| 5,165,407 | A | 11/1992 | Wilson et al. |
| 5,200,334 | A | 4/1993 | Dunn et al. |
| 5,292,801 | A | 3/1994 | Avnir et al. |
| 5,300,564 | A | 4/1994 | Avnir et al. |
| 5,342,789 | A | 8/1994 | Chick et al. |
| 5,445,920 | A | 8/1995 | Saito |
| 5,501,836 | A | 3/1996 | Myerson |
| 5,517,313 | A | 5/1996 | Colvin, Jr. |
| 5,577,137 | A | 11/1996 | Groger et al. |
| 5,650,311 | A | 7/1997 | Avnir et al. |
| 5,817,493 | A | 10/1998 | Reetz et al. |
| 5,824,526 | A | 10/1998 | Avnir et al. |
| 5,894,351 | A | 4/1999 | Colvin, Jr. |
| 5,910,661 | A | 6/1999 | Colvin, Jr. |
| 6,016,689 | A | 1/2000 | Bright et al. |
| 6,080,402 | A | 6/2000 | Reetz et al. |
| 6,197,534 | B1 | 3/2001 | Lakowicz et al. |
| 6,277,627 | B1 | 8/2001 | Hellinga |
| 6,288,214 | B1 | 9/2001 | Hook et al. |
| 6,403,337 | B1 | 6/2002 | Bailey et al. |
| 6,432,723 | B1 | 8/2002 | Plaxco et al. |
| 6,521,446 | B2 * | 2/2003 | Hellinga .................. 435/287.1 |
| 2002/0004217 | A1 | 1/2002 | Hellinga |
| 2003/0104595 | A1 * | 6/2003 | Kratzch et al. ............. 435/189 |
| 2003/0130167 | A1 * | 7/2003 | Pitner et al. .................... 514/2 |
| 2003/0153026 | A1 * | 8/2003 | Alarcon et al. ............... 435/14 |

FOREIGN PATENT DOCUMENTS

| EP | 0 775 669 B1 | 11/1996 |
|---|---|---|
| WO | WO 00/59370 | 10/2000 |

OTHER PUBLICATIONS

Baird et al., Current and Emerging Commerical Optical Biosensors, J. Mol. Recognit. 2001; 14:261–268.

Bhatia et al., Optical Fiber Long–Period Grating Sensors, Optics Letters, vol. 21, No. 9, May 1, 1996.

Gilardi, et al., Engineering the Maltose Binding Protein for Reagentless Fluorescence Sensing, Anal. Chem., 1994, 66, 3840–3847.

Jones, et al., Bioremediation Monitoring Using Optical Fiber Long Period Grating (LPG)–Based Sensors, NFS Manufacturing Conference, Vancouver, Jan., 2000.

Marvin, et al., Engineering Biosensors by Introducing Fluorescent Allosteric Signal Transducers: Construction of a Novel Glucose Sensor, J. Am. Chem. Soc. 1998, 120, pp. 7–11.

Marvin et al., The Rational Design Of Allosteric Interactions In A Monomeric Protein And Its Applications To The Construction Of Biosensors, Proc. Natl. Acad. Sci. USA, vol. 99, pp. 436–4371, Apr. 1997 Biochemistry.

Mowbray, et al., Structure of the Periplasmic Glucose/Galactose Receptor of Salmonella Typhimurium, Receptor, 1990, I, pp. 41–54.

Pisarchick et al., Binding of A Monoclonal Antibody and its Fab Fragment to Supported Phospholipid Monolayers Measured By Total Internal Reflection Fluorescence Microscopy, Biophys. J., Biophysical Society, vol. 58, Nov. 1990, pp. 1235–1249.

Salins et al., Reagentless Optical Detection Of Glucose Using Genetically Engineered Galactose/Glucose Binding Protein, Abstracts of Papers of the Americal Chemical Society, 219: 162–BIOL, Part I Mar. 26, 2000.

Salins et al., Reagentless Optical Detection Of Glucose Using Genetically Engineered Galactose/Glucose Binding Protein, Biochemistry 39 (6): 162 Feb. 15, 2000.

Tolosa, et al., Glucose Sensor for Low–Cost Lifetime–Based Sensing Using A Genetically Engineered Protein, Analytical Biochemistry 267, pp. 114–120 (1999).

Tolosa, et al., Optical Biosensors Based On Genetically–Engineered E. coli Periplasmic Binding Proteins, Biophys. J. 2000 (Jan.) p. 416A.

Topoglidis, et al., Protein Adsorption on Nanocrystalline TiO2 Films: An Immobilization Strategy for Bioanalytical Devices, Anal. Chem. 1998, 70, pp. 5111–5113.

O'Sullivan, et al., Commercial Quartz Crystal Microbalances—Theory and Applications, Biosensors & Bioelectronics 14 (1999) pp. 663–670.

(List continued on next page.)

Primary Examiner—Lyle A. Alexander

(57) ABSTRACT

The invention is directed to compositions of mutated binding proteins containing reporter groups, analyte biosensor devices derived there from, and their use as analyte biosensor both in vitro and in vivo.

21 Claims, 3 Drawing Sheets

OTHER PUBLICATIONS

Turcatti, et al., Probing the Structure and Function of the Tachykinin Neurokinin–2 Receptor through Biosenthetic Incorporation of Fluorescent Amino Acids at Specific Sites, The Journal of Biological Chemistry, vol. 271, No. 33, Isuse of Aug. 16, pp. 19991–19998, 1996.

Vyas, et al., Sugar and Signal–Transducer Binding Sites of the *Escherichia coli* Galactose Chemoreceptor Protein, Science, vol. 242 pp. 1290–1295 (Dec., 1998).

Avnir, et al., Encapsulation of Organic Molecules and Enzymes In Sol–Gel Glasses, A Review of Novel Photoactive, Optical, Sensing, and Bioactive Materials, ACS Symposium Series 1992, 499, p. 384–404.

Avnir, et al., Enzymes and Ohter Proteins Entrapped in Sol–Gel Materials, Chem. Mater. 1994, 6, p. 1605–1614.

Baker, et al., Effects of Poly (theylene glycol) Doping on the Behavior of Pyrene, Rhodamine 6G, and Acrylodan–Labeled Bovine Serum Albumin Sequestered within Tetramethylorthosilane–Derived Sol–Gel–Process Composites, Journal of Sol–Gel Science and Tech. 11, p 43–54 (1998).

Beach, et al., Subminiature Implantable Potentiostat and Modified Commercial Telemetry Device for Remote Glucose Monitoring, IEEE Transactions on Instrumentation and Measurement 1999, 48, p. 1239–1245.

Braun, et al., Biochemically Active Sol–Gel Glasses: The Trapping of Enzymes, Materials Letters, vol. 10, No. 1,2, (1990) p. 1–5.

Brennan, et al., Preparation and Entrapment of Fluorescently Labeled Proteins for the Development of Reagentless Optical Biosensors, Journal of Fluorescence, vol. 9, No. 4 (1999) p. 295–312.

Dave, et al., Encapsulation of Proteins in Bulk and Thin Film Sol–Gel Matrices, Journal of Sol–Gel Science and Technology 8 (1997) p. 629–634.

Flora, et al., Comparison of Formats For The Development of Fiber–Optic Biosensors Utilizing Sol–Gel Derived Materials Entrapping Fluorescently–Labelled Protein, Analyst 124 ( 1999) p. 1455–1462.

Flora, et al., The Effect Of Preparation and Aging Conditions On The Internal Environment Of Sol–Gel Derived Materials As Probed by 7–Azaindole and Pyranine Fluorescence, Can. J. Chem. 77 (1999) p. 1617–1625.

Flora, et al., Effect of Matrix Aging on the Behavior of Human Serum Albumin Entrapped in a Tetraethyl Orthosilicate–Derived Glass, Chem. Mater. 13 (2001) p. 4170–4179.

Flora, et al. Fluorometric Detection of Ca2+ Based on an Induced Change in the Conformation of Sol–Gel Entrapped Parvalbumin, Anal. Chem. 70 (1998) p. 4504–4513.

Gerritsen, et al., Biocompatibility Evaluation of Sol–Gel Coatings For Subcutaneously Implantable Glucose Sensors, Biomaterials 21 (2000) p. 71–78.

Gill, et al., Encapsulation of Biologicals Within Silocate, Siloxane, and Hybrid Sol–Gel Polymers: An Effecient and Generic Approach, J. Am. Chem. Soc. 120 (1998) p. 8587–8598.

Gill, et al., Novel Sol–Gel Matrices for the Immobiliation of Enzymes, Annals New York Academy of Sciences 799 (1996) p. 697–700.

Gowda, et al., Development of an Implantable Skin Port Sensor For Use As An In Vitro Optical Glucose Sensing Platform, Optical Diagnostics and Sensing of Biological Fluids and Glucose and Cholesterol Monitoring, Proc. SPIE vol. 4263 (2001) p. 11–19.

Narang, et al., Glucose Biosensor Based on a Sol–Gel–Derived Platform, Anal. Chem. 66 (1994) p. 3139–3144.

O'Neal, et al., Implantable Biosensors: Analysis of Fluorescent Light Propagation Through Skin, Optical Diagnostics and Sensing of Biological Fluids and Glucose and Cholesterol Monitoring, Proc. of SPIE vol. 4263 (1002) p. 20–24.

Shtelzer, et al., An Optical Biosensor Based Upon Glucose Oxidase Immobilized In Sol–Gel Silicate Matrix, Biotechnol. Appl. Biochem 19 (1994) p. 293–305.

Tsionsky, et al., Organically Modified Sol–Gel Sensors, Analytical Chemistry vol. 67, No. 1 (1995) p. 22–30.

Zheng, et al., Improving the Performance of a Sol–Gel–Entrapped Metal–Binding Protein by Maximizing Protein Thermal Stability Before Entrapment, Chem. Mater. 10 (1998) p. 3974–3983.

Zheng, et al., Measurement of Fluorescence from Typtophan To Probe The Environment and Reaction Kinetics Within Protein–Doped Sol–Gel–Derived Blass Monoliths, Anal. Chem. 69 (1997) p. 3940–3949.

Zheng, et al., Measurement of Intrinsic Fluorescence To Probe The Conformational Flexibility and Thermodynamic Stability of a Single Tryptophan Protein Entrapped In A Sol–Gel Derived Blass Matrix, Analyst. vol. 123 (1998) p. 1735–1744.

Zusman, et al., Doped Sol–Gel Glasses As Chemical Sensors, Journal of Non–Crystalline Solids 122 (1990) p. 107–109.

* cited by examiner

BINDING PROTEIN AS BIOSENSORS

BACKGROUND OF THE INVENTION

1. Field of the Invention

The invention is in the field of biotechnology. Specifically, the invention is directed to compositions of mutated binding proteins containing reporter groups, analyte biosensor devices derived there from, and their use as analyte biosensors both in vitro and in vivo.

2. Description of Relevant Art

Monitoring glucose concentrations to facilitate adequate metabolic control in diabetics is a desirable goal and would enhance the lives of many individuals. Currently, most diabetics use the "finger stick" method to monitor their blood glucose levels and patient compliance is problematic due to pain caused by frequent (several times per day) sticks. As a consequence, there have been efforts to develop non-invasive or minimally invasive in vivo and more efficient in vitro methods for frequent and/or continuous monitoring of blood glucose or other glucose-containing biological fluids. Some of the most promising of these methods involve the use of a biosensor. Biosensors are devices capable of providing specific quantitative or semi-quantitative analytical information using a biological recognition element which is combined with a transducing (detecting) element.

The biological recognition element of a biosensor determines the selectivity, so that only the compound which has to be measured leads to a signal. The selection may be based on biochemical recognition of the ligand where the chemical structure of the ligand (e.g. glucose) is unchanged, or biocatalysis in which the element catalyzes a biochemical reaction of the analyte.

The transducer translates the recognition of the biological recognition element into a semi-quantitative or quantitative signal. Possible transducer technologies are optical, electrochemical, acoustical/mechanical or colorimetrical. The optical properties that have been exploited include absorbance, fluorescence/phosphorescence, bio/chemiluminescence, reflectance, light scattering and refractive index. Conventional reporter groups such as fluorescent compounds may be used, or alternatively, there is the opportunity for direct optical detection, without the need for a label.

Biosensors specifically designed for glucose detection that use biological elements for signal transduction typically use electrochemical or calorimetric detection of glucose oxidase activity. This method is associated with difficulties including the influence of oxygen levels, inhibitors in the blood and problems with electrodes. In addition, detection results in consumption of the analyte that can cause difficulties when measuring low glucose concentrations.

A rapidly advancing area of biosensor development is the use of fluorescently labeled periplasmic binding proteins (PBP's). As reported by Cass (Anal. Chem. 1994, 66, 3840–3847), a labeled maltose binding protein (MBP) was effectively demonstrated as a useable maltose sensor. In this work MBP, which has no native cysteine residues, was mutated to provide a protein with a single cysteine residue at a position at 337 (S337C). This mutation position was within the binding cleft where maltose binding occurred and therefore experienced a large environmental change upon maltose binding. Numerous fluorophores were studied, some either blocked ligand binding or interfered with the conformational change of the protein. Of those studied IANBD resulted in a substantial increase in fluorescence (160%) intensity upon maltose binding. This result may be consistent with the location of the fluorophore changing from a hydrophilic or solvent exposed environment to a more hydrophobic environment as would have been theoretically predicted for the closing of the hinge upon maltose binding. However this mutant protein and the associated reporter group do not bind diagnostically important sugars in mammalian bodily fluids. Cass also disclosed (Analytical Chemistry 1998, 70(23), 5111–5113) association of this protein onto TiO2 surfaces, however, the surface-bound protein suffered from reduced activity with time and required constant hydration.

Hellinga, et al. (U.S. Pat. No. 6,277,627), reports the engineering of a glucose biosensor by introducing a fluorescent transducer into a Galactose/Glucose Binding Protein (GGBP) mutated to contain a cysteine residue, taking advantage of the large conformation changes that occur upon glucose binding. Hellinga et al (U.S. Pat. No. 6,277,627) disclose that the transmission of conformational changes in mutated GGBPs can be exploited to construct integrated signal transduction functions that convert a glucose binding event into a change in fluorescence via an allosteric coupling mechanism. The fluorescent transduction functions are reported to interfere minimally with the intrinsic binding properties of the sugar binding pocket in GGBP.

In order to accurately determine glucose concentration in biological solutions such as blood, interstitial fluids, occular solutions or perspiration, etc., it may be desirable to adjust the binding constant of the sensing molecule of a biosensor so as to match the physiological and/or pathological operating range of the biological solution of interest. Without the appropriate binding constant, a signal may be out of range for a particular physiological and/or pathological concentration. Additionally, biosensors may be configured using more than one protein, each with a different binding constant, to provide accurate measurements over a wide range of glucose concentrations as disclosed by Lakowicz (U.S. Pat. No. 6,197,534).

Despite the usefulness of mutated GGBPs, few of these proteins have been designed and examined, either with or without reporter groups. Specific mutations of sites and/or attachment of certain reporter groups may act to modify a binding constant in an unpredictable way. Additionally, a biosensor containing reporter groups may have a desirable binding constant, but not result in an easily detectable signal change upon analyte binding. Some of the overriding factors that determine sensitivity of a particular reporter probe attached to a particular protein for the detection of a specific analyte is the nature of the specific interactions between the selected probe and amino acid residues of the protein. It is not currently possible to predict these interactions within proteins using existing computational methods, nor is it possible to employ rational design methodology to optimize the choice of reporter probes. It is currently not possible to predict the effect on either the binding constant or the selectivity based on the position of any reporter group, or amino acid substitution in the protein (or visa-versa).

To develop reagentless, self-contained, and or implantable and or reusable biosensors using proteins the transduction element must be in communication with a detection device to interrogate the signal to and from the transduction element. Typical methods include placing proteins within or onto the surface of optical fibers or planner waveguides using immobilization strategies. Such immobilization strategies include entrapment of the protein within semipermeable membranes, organic polymer matrixes, or inorganic polymer matrixes. The immobilization strategy ultimately may determine the performance of the working biosensor. Prior art details numerous problems associated with the immobilization of biological molecules. For example, many proteins undergo irreversible conformational changes, denaturing, and loss of biochemical activity. Immobilized proteins can exist in a large number of possible orientations on any particular surface, for example, with some proteins oriented such that their active sites are exposed whereas others may be oriented such that there active sites are not exposed, and thus not able to undergo selective binding reactions with the analyte. Immobilized proteins are also subject to time-dependent denaturing, denaturing during immobilization, and leaching of the entrapped protein subsequent to immobilization. Therefore, problems result including an inability to maintain calibration of the sensing device and signal drift. In general, binding proteins require orientational control to enable their use, thus physical absorption and random or bulk covalent surface attachment or immobilization strategies as taught in the literature generally are not successful.

Therefore, there is a need in the art to design additional useful mutated proteins and mutated GGBP proteins generating detectable signal changes upon analyte binding for use as biosensors, and additionally there is a need in the art to design additional useful mutated binding protein and mutated GGBPs containing reporter groups generating detectable and reversible signal changes upon analyte or glucose binding for use as biosensors.

SUMMARY OF THE INVENTION

Figure 1:
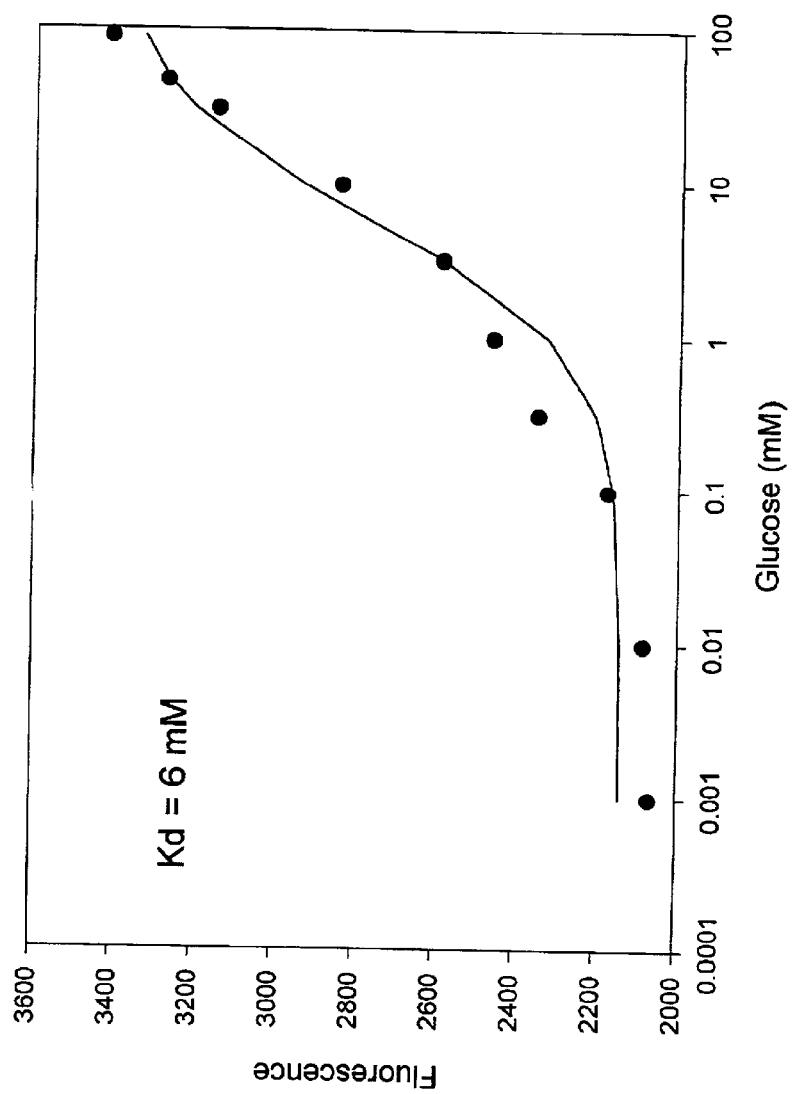
FIG. 1 illustrates the change in fluorescence response to a range of glucose concentrations for A213C/L238C NBD amide GGBP $H_6$ in solution.

The invention provides a glucose biosensor for in vivo or in vitro use having a) at least one mutated binding protein and at least one reporter group attached thereto such that said reporter group provides a detectable and reversible signal change when said mutated binding protein is exposed to varying glucose concentrations; wherein said detectable and reversible signal change is related to said varying concentrations.

Furthermore, the invention provides a method for glucose detection including a) providing at least one mutated glucose/galactose binding protein and at least one reporter group attached thereto; b) exposing said mutated glucose/galactose binding protein to varying glucose concentrations; c) detecting a detectable and reversible signal change from said reporter group wherein said detectable and reversible signal change corresponds to said varying glucose concentrations.

The invention additionally provides a composition including a mutated glucose/galactose binding protein having at least one amino acid substitution selected from the group consisting of a cysteine at position 11, a cysteine at position 14, a cysteine at position 19, a cysteine at position 43, a cysteine at position 74, a cysteine at position 107, a cysteine at position 110, a cysteine at position 112, a cysteine at position 113, a cysteine at position 137, a cysteine at position 149, a cysteine at position 213, a cysteine at position 216, a cysteine at position 238, a cysteine at position 287, and a cysteine at position 292.

Also, provided herein is a composition having a mutated glucose/galactose binding protein having at least two amino acid substitutions selected from the group consisting of a cysteine at position 112 and a serine at position 238, a cysteine at position 149 and a serine at position 238, a cysteine at position 152 and a cysteine at position 182, a cysteine at position 152 and a serine at position 213, a cysteine at position 213 and a cysteine at position 238, a cysteine at position 149 and an arginine at position 213, and a cysteine at position 149 and a serine at position 213 and a serine at position 238, and a cysteine at position 149 and an arginine at position 213 and a serine at position 238.

DETAILED DESCRIPTION

The term biosensor generally refers to a device that uses specific biochemical reactions mediated by isolated enzymes, immunosystems, tissues, organelles or whole cells to detect chemical compounds, usually by electrical, thermal or optical signals. As used herein a "biosensor" refers to a protein capable of binding to an analyte which may be used to detect an analyte or a change in analyte concentration by a detector means as herein described.

The term "binding proteins" refers to proteins which interact with specific analytes in a manner capable of providing or transducing a detectable and/or reversible signal differentiable either from when analyte is not present, analyte is present in varying concentrations over time, or in a concentration-dependent manner, by means of the methods described herein. The transduction event includes continuous, programmed, and episodic means, including one-time or reusable applications. Reversible signal transduction may be instantaneous or may be time-dependent providing a correlation with the presence or concentration of analyte is established. Binding proteins mutated in such a manner to effect transduction are preferred.

The term "Galactose/Glucose Binding Protein" or "GGBP" as used herein refers to a type of protein naturally found in the periplasmic compartment of bacteria. These proteins are naturally involved in chemotaxis and transport of small molecules (e.g., sugars, amino acids, and small peptides) into the cytoplasm. GGBP is a single chain protein consisting of two globular α/β domains that are connected by three strands to form a hinge. The binding site is located in the cleft between the two domains. When glucose enters the binding site, GGBP undergoes a conformational change, centered at the hinge, which brings the two domains together and entraps glucose in the binding site. X-ray crystallographic structures have been determined for the closed form of GGBP from E. coli (N. K. Vyas, M. N. Vyas, F. A. Quiocho Science 1988, 242, 1290–1295) and S. Typhimurium (S. L. Mowbray, R. D. Smith, L. B. Cole Receptor 1990, 1, 41–54) and are available from the Protein Data Bank (http://www.rcsb.org/pdb/) as 2GBP and 3GBP, respectively. The wild type E. coli GGBP DNA and amino acid sequence can be found at www.ncbi.nlm.nih.gov/entrez/ accession number D90885 (genomic clone) and accession number 23052 (amino acid sequence). Preferred GGBP is from E. coli.

"Mutated Binding Protein" (for example "mutated GGBP") as used herein refers to binding proteins from bacteria containing an amino acid(s) which has been substituted for, deleted from, or added to the amino acid(s) present in naturally occurring protein.

Exemplary mutations of binding proteins include the addition or substitution of cysteine groups, non-naturally occurring amino acids (Turcatti, et al. *J. Bio. Chem.* 1996 271, 33, 19991–19998) and replacement of substantially non-reactive amino acids with reactive amino acids to provide for the covalent attachment of electrochemical or photo-responsive reporter groups.

Exemplary mutations of the GGBP protein include a cysteine substituted for a lysine at position 11 (K11C), a cysteine substituted for aspartic acid at position 14 (D14C), a cysteine substituted for valine at position 19 (V19C), a cysteine substituted for asparagine at position 43 (N43C), a cysteine substituted for a glycine at position 74 (G74C), a cysteine substituted for a tyrosine at position 107 (Y107C), a cysteine substituted for threonine at position 110 (T110C), a cysteine substituted for serine at position 112 (S112C), a double mutant including a cysteine substituted for a serine at position 112 and serine substituted for an leucine at position 238(S112C/L238S), a cysteine substituted for a lysine at position 113 (K113C), a cysteine substituted for a lysine at position 137 (K137C), a cysteine substituted for glutamic acid at position 149 (E149C), a double mutant including a cysteine substituted for an glutamic acid at position 149 and a serine substituted for leucine at position 238 (E149C/L238S), a double mutant comprising a cysteine substituted for histidine at position 152 and a cysteine substituted for methionine at position 182 (H152C/M182C), a double mutant including a serine substituted for an alanine at position 213 and a cysteine substituted for a histidine at position 152 (H152C/A213S), a cysteine substituted for an methionine at position 182 (M182C), a cysteine substituted for an alanine at position 213 (A213C), a double mutant including a cysteine substituted for an alanine at position 213 and a cysteine substituted for an leucine at position 238 (A213C/L238C), a cysteine substituted for an methionine at position 216 (M216C), a cysteine substituted for aspartic acid at position 236 (D236C), a cysteine substituted for an leucine at position 238 (L238C) a cysteine substituted for a aspartic acid at position 287 (D287C), a cysteine substituted for an arginine at position 292 (R292C), a cysteine substituted for a valine at position 296 (V296C), a triple mutant including a cysteine substituted for an glutamic acid at position 149 and a alanine substituted for a serine at position 213 and a serine substituted for leucine at position 238 (E149C/A213S/L238S), a triple mutant including a cysteine substituted for an glutamic acid at position 149 and a alanine substituted for an arginine at position 213 and a serine substituted for leucine at position 238 (E149C/A213R/L238S).

The mutation may serve one or more of several purposes. For example, a naturally occurring protein may be mutated in order to change the long-term stability of the protein; to conjugate the protein to a particular encapsulation matrix, polymer; or to provide binding sites for detectable reporter groups, or to adjust its binding constant with respect to a particular analyte, and combinations thereof.

In the instant invention, analyte and mutated protein act as binding partners. The term "associates" or "binds" as used herein refers to binding partners having a relative binding constant (Kd) sufficiently strong to allow detection of binding to the protein by a detection means. The Kd may be calculated as the concentration of free analyte at which half the protein is bound, or vice versa. When the analyte of interest is glucose, the Kd values for the binding partners are preferably between about 0.0001 mM to about 20 mM, more preferably, the Kd values range from about 1 mM to 10 mM in the instant invention.

In the present invention, it has been shown that mutated GGBPs may be used to detect glucose binding by attaching thereto a reporter group which tranduces a detectable signal change upon glucose binding. To "provide a detectable signal change", as used herein refers to the ability to recognize a change in a property of a reporter group in a manner that enables the detection of ligand-protein binding. For example, in one embodiment, the mutated GGBPs comprise a detectable reporter group whose detectable characteristics alter upon a change in protein conformation which occurs on glucose binding. In a preferred embodiment, the reporter group is a luminescent label which results in a mutated GGBP with an affinity for glucose producing a detectable shift in luminescence characteristics on glucose binding. The change in the detectable characteristics may be due to an alteration in the environment of the label, which is bound to the mutated GGBP.

The luminescent label may be a fluorescent label or a phosphorescent label. The use of fluorescent labels, which may be excited to fluoresce by exposure to certain wavelengths of light is preferred.

In one embodiment, the reporter group is a fluorophore. As used herein, "fluorophore" refers to a molecule that absorbs energy and then emits light. Non-limiting examples of fluorophores useful as reporter groups in this invention include fluorescein, coumarins, rhodamines, 5-TMRIA (tetramethylrhodamine-5-iodoacetamide), Quantum Red™, Texas Red™, Cy3, N-((2-iodoacetoxy)ethyl)-N-methyl) amino-7-nitrobenzoxadiazole (IANBD), 6-acryloyl-2-dimethylaminonaphthalene (acrylodan), pyrene, Lucifer Yellow, Cy5, Dapoxyl® (2-bromoacetamidoethyl) sulfonamide, (N-(4,4-difluoro-1,3,5,7-tetramethyl-4-bora-3a,4a-diaza-s-indacene-2-yl) (Bodipy507/545 IA), N-(4,4-difluoro-5,7-diphenyl-4-bora-3a,4a-diaza-s-indacene-3-propionyl)-N'-iodoacetylethylenediamine (BODIPY®530/550 IA), 5-((((2-iodoacetyl)amino)ethyl) amino) naphthalene-1-sulfonic acid (1,5-IAEDANS), and carboxy-X-rhodamine, 5/6-iodoacetamide (XRIA 5,6). Preferably, IANBD is used. Many detectable intrinsic properties of a fluorophore reporter group may be monitored to detect glucose binding. Some of these properties which can exhibit changes upon glucose binding include fluorescence lifetime, fluorescence intensity, fluorescence anisotropy or polarization, and spectral shifts of fluorescence emission. Changes in these fluorophore properties may be induced from changes in the fluorophore environment such as those resulting from changes in protein conformation. Environment-sensitive dyes such as IANBD are particularly useful in this respect. Other changes of fluorophore properties may result from interactions with the analyte itself or from interactions with a second reporter group, for example when FRET (fluorescence resonance energy transfer) is used to monitor changes in distance between two fluorophores.

Although the use of fluorescent labels is desired, it is contemplated that other reporter groups may be used. For example, electrochemical reporter groups could be used wherein an alteration in the environment of the reporter will give rise to a change in the redox state thereof. Such a change may be detected using an electrode.

Furthermore, it is envisaged that other spectroscopically detectable labels, for example labels detectable by NMR (nuclear magnetic resonance), may be used, as are known in the art.

The reporter group may be attached to the mutated protein or GGBPs by any conventional means known in the art. For example, the reporter group may be attached via amines or carboxyl residues on the protein. However, especially preferred is covalent coupling via thiol groups on cysteine residues. For example, for mutated GGBP, cysteines located at position 11, position 14, position 19, position 43, position 74, position 107, position 110, position 112, position 113, position 137, position 149, position 152, position 213, position 216, position 238, position 287, and position 292 are preferred in the present invention.

Any thiol-reactive group known in the art may be used for attaching reporter groups such as fluorophores to an engineered protein's cysteine. For example, an iodoacetamide bromoacetamide, or maleimide are well known thiol-reactive moieties which may be used for this purpose.

Fluorophores that operate at long excitation and emission wavelengths (for example, about 600 nm or greater exitation or emmision wavelengths) are preferred when the molecular sensor is to be used in vivo, for example, incorporated into an implantable biosensor device (the skin being opaque below 600 nm). Presently, there are few environmentally sensitive probes available in this region of the spectrum and perhaps none with thiol-reactive functional groups. However, thiol-reactive derivatives of Cy-5 can be prepared for example as taught by H. J. Gruber, et al, *Bioconjugate Chem.*, (2000), 11, 161–166. Conjugates containing these fluorophores, for example, attached at various cysteine mutants constructed in mutated GGBPs, can be screened to identify those which result in the largest change in fluorescence upon glucose binding.

Mutated GGBPs may be engineered to have a histidine tag on the proteins N-terminus, C-terminus, or both termini. Histidine fusion proteins are widely used in the molecular biology field to aid in the purification of proteins. Exemplary tagging systems produce proteins with a tag containing about six histidines and preferably such tagging does not compromise the binding activity of the mutated GGBP.

The present invention also provides a biosensor and method of using the biosensor for analyte sensing in vivo. In this aspect, the biosensor is comprised of one or more mutated binding proteins which are encapsulated into a matrix. The encapsulated biosensor may then be used as an implantable device or part thereof.

The "matrix" can be in any desirable form or shape including a disk, cylinder, patch, microsphere, porous polymer, open cell foam or the like, providing it permits permeability to analyte. The matrix additionally prevents leaching of the biosensor. The matrix permits light from optical sources or any other interrogating light to or from the reporter group to pass through the biosensor. When used in an in vivo application, the biosensor will be exposed to a physiological range of analyte. The means of determination or detection of a change in analyte concentration may, in one embodiment, be continuous. Alternatively, the means of determination or detection of analyte concentration may be programmed or episodic.

The envisioned in vivo biosensor of the present invention comprises at least one mutated binding protein in an analyte permeable entrapping or encapsulating matrix such that the mutated binding protein provides a detectable and reversible signal change when the mutated binding protein is exposed to varying analyte concentrations, and the detectable and reversible signal can be related to the concentration of the analyte.

In this aspect of the invention, the configuration of the transducing element may be, for example, incorporated at the distal end of a fiber or other small minimally invasive probe and be inserted within the tissue of a patient to enable methods of use including episodic, continuous, or programmed reading to the patient. The implantable biosensors may, in some embodiments, be implanted into or below the skin of a mammal's epidermal-dermal junction to interact with the interstitial fluid, tissue, or other biological fluids.

An exemplary method which may be used to detect the presence of analyte using the biosensor for in vivo use described herein includes interrogating the implant with a remote light source, detecting the signal from the protein-reporter group, and determining the amount of glucose based on a relationship to the detected signal as is known in the art (see U.S. Pat. No. 5,517,313, U.S. Pat. No. 5,910,661, and U.S. Pat. No. 5,342,789, all of which are herein incorporated by reference).

The binding protein biosensors of this invention are capable of measuring or detecting micromolar ($10^{-6}$ molar) to molar analyte concentrations without reagent consumption. In some embodiments, their sensitivity to analyte may enable the biosensors to be used to measure the low analyte concentrations known to be present in low volume samples of interstitial or ocular fluid and perspiration. The binding protein biosensors of the present invention provide for the means to monitor analyte continuously, episodically, or "on-demand" as would be appropriate to the user or to the treatment of a condition.

In other embodiments, the biosensors sensitivity to analyte (for example glucose) is such that they may be used to test blood analyte levels or the concentration of analyte in a biological solution or other solution may be determined. As used herein, a "biological solution" includes but is not limited to blood, perspiration, and/or ocular or interstitial fluid including combinations thereof.

The following examples illustrate certain preferred embodiments of the instant invention, but are not intended to be illustrative of all embodiments.

This example describes the method for the expression and purification of mutant Proteins Without Histidine Tags.

GGBP is coded by the Mg1B-1 gene in *E. coli*. This protein was altered by introducing the amino acid cysteine at various positions through site-directed mutagenesis of the Mg1B-1 gene. These proteins were then expressed in *E. coli* and purified.

Cassette mutagenesis of Mg1B-1 was accomplished as follows. The wild-type Mg1B-1 gene was cloned into a pTZ18R vector (Dr. Anthony Cass, Imperial College, London, England). Mutant plasmids were generated from this parent plasmid using cassette mutatgenesis producing randomized amino acid sequences, essentially as described by Kunkel (1991) and cloned in *E. coli* JM109 (Promega Life Science, Madison, Wis.). Mutant plasmids were identified by sequencing. The mutant protein was induced in JM109 and purified as described below. An *E. coli* JM109 colony containing the mutant plasmid was grown overnight at 37° C. with shaking (220 rpm) in LB broth containing 50 μg/mL ampicillin (LB/Amp). The overnight growth was diluted 1:100 in 1 L fresh LB/Amp and was incubated at 37° C. with shaking until the $OD_{600}$ of the culture was 0.3–0.5. Expression of the mutant was induced by the addition of 1 mM IPTG (Life Technologies, Gaithersburg, Md.) final concentration with continued incubation and shaking at 37° C. for 4–6 hours. The cells were harvested by centrifugation (10,000×g, 10 min, 4° C.).

The mutant protein was harvested by osmotic shock and was purified by column chromatography. The cell pellet was resuspended in a sucrose buffer (30 mM Tris-HCL pH 8.0, 20% sucrose, 1 mM EDTA), incubated at room temperature for 10 min, and then centrifuged (4000×g, 15 min, 4° C.). The supernatant was poured off and kept on ice. The cell pellet was resuspended, and 10 mL ice cold, sterile deionized $H_2O$ was repeated, and the suspension was incubated on ice and centrifuged. The remaining supernatant was pooled with the other collected supernatants and was centrifuged once again (12,000×g, 10 min, 4° C.). The pooled shockate was filtered through a 0.8 μm and then a 0.45 μm filter. Streptomycin sulfate (Sigma Chemical Co., St. Louis, Mo.), 5% w/v, was added to the shockate and was stirred once for 30 min followed by centrifugation (12,000×g, 10 min, 4° C.). The shockate was then concentrated using the Amicon Centriprep 10 (10,000 MWCO) filters (Charlotte, N.C.) and dialyzed overnight against 5 mM Tris-HCl pH 8.0, 1 mM $MgCl_2$. The dialyzed shockate was centrifuged (12,000 ×g, 30 min, 4° C.). The resulting supernatant was added to a pre-equilibrated DEAE Fast Flow Sepharose column (Amersham Pharmacia Biotech, Piscataway, N.J.) at 0.5 mL/min. The column was washed with 5–10 column volumes. A linear gradient from 0–0.2 M NaCl was applied to the column and fractions were collected. The mutant protein containing fractions were identified by SDS-PAGE with Coomassie Brilliant Blue staining (mw. Approx. 32 kDa). The fractions were pooled and dialyzed overnight (4° C.) against phosphate buffered saline (PBS) or 10 mM ammonium bicarbonate (pH 7.4) concentrated using Amicon Centriprep 10 filters, and stored at 4° C. or −20° C. with glycerol. The ammonium bicarbonate dialyzed protein was lyophilized.

This example describes the expression and purification of mutant GGBPs containing Histidine Tags.

GGBP mutants were engineered by either site-directed mutagenesis or the cassette mutagenesis. Site-directed mutagenesis (QuikChange, Stratagene, La Jolla, Calif.) was performed to alter individual amino acids in the pQE70 vector by replacing one amino acid with another, specifically chosen amino acid. The cassette mutagenesis method (Kunkel 1991) was performed to randomize amino acids in a specified region of the GGBP gene. The mutated cassettes were then subcloned into the pQE70 expression vector.

The pGGBP-His plasmid contained the GGBP gene cloned into the pQE70 expression vector (Qiagen, Valencia, Calif.). This construct places six histidine residues on the C-terminus of the GGBP gene. *E. coli* strain SG13009 was used to over express mutant GGBP-His following standard procedures (Qiagen). After over expression of a 250 mL culture, the cells were collected by centrifugation (6000 rpm) and resuspended in 25 mL bugbuster (Novagen, Madison, Wis.). Lysozyme (25 mg was added to the lysate and the mixture was gently mixed at room temperature (RT) for 30 min. Clear lysate was produced by centrifugation (6000 rpm) and to this, 0.5 ml imidizole (1 M) and 3 ml of Ni-NTA beads (Qiagen) was added. After 30 minutes of gently mixing at RT, the mixture was centrifuged (6000 rpm) and the lysate removed. The beads were washed with 25 ml of solution (1M NaCl, 10 mM tris, pH 8.0) and recentrifuged. The mutant GGBP-His was eluted from the beads by adding 5 mL solution (160 mM imidazole, 1 M NaCl, 10 mM Tris, pH 8.0) and mixing for 15 min. The protein solution was immediately filtered through a Centriplus YM-100 filter (Amicon, Charlotte, N.C.) and then concentrated to 1–3 mg/ml using a Centriplus YM-10 filter. The protein was dialyzed overnight against 2 L of storage solution (1 M NaCl, 10 mM Tris, 50 mM $NaPO_4$, pH 8.0).

Figure 2:
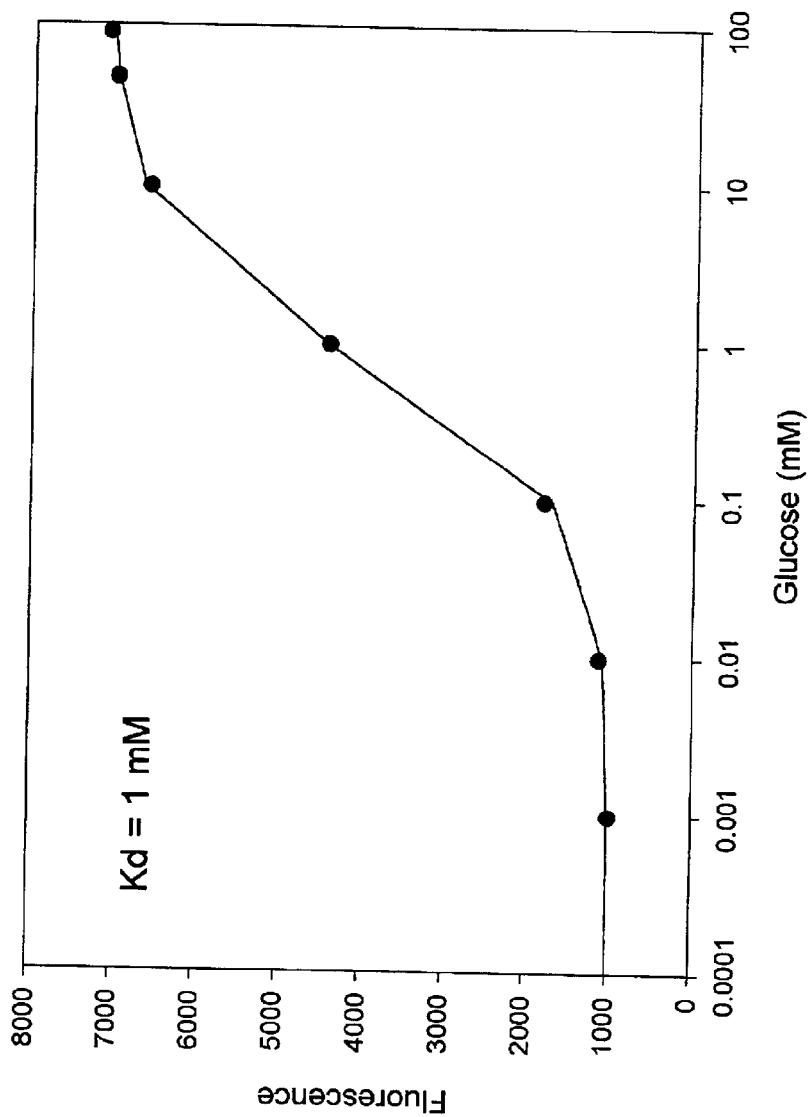
FIG. 2 illustrates the change in fluorescence response to a range of glucose concentrations for E149C/A213R NBD amide GGBP $H_6$ in solution.

This example describes how the mutant GGBPs were labeled. An aliquot of mutant GGBP containing cysteine (4.0 nmol) in PBS was treated with 2 mM dithiothreitol (5 μL, 10 nmol) for 30 min. A stock solution of N,N'-dimethyl-N-(iodoacetyl)-N'-(7-nitrobenzyl-2-oxa-1,3-diazol-4-yl) ethylenodiamine (IANBD amide, 0.5 mg) was prepared in DMSO (100 μL, 11.9 mM) and 3.36 μL (40 nmol) was added to the protein. The reaction proceeded at room temperature for 4 h on a Dynal rotamix in the dark. The labeled protein was purified by gel filtration on a NAP-5 column (Amersham Pharmacia). The labeling ratios were determined using an estimated extinction coefficient (50 $mM^{-1}$ $cm^{-1}$) for GGBP that was calculated in GeneWorks 2.45 (IntelliGenetics), $_{478}$(IANBD amide)=25 $mM^{-1}$ $cm^{-1}$), and a measurement of O.D. for a standard solution of IANBD amide at 280 nm and 478 nm. The dye concentration in the protein was calculated as $C_{dye}=478/A_{478}$. The absorbance of protein at 280 nm was calculated as $A_{prot(280)}=A_{total(280)}-A_{dye(280)}$, where $A_{dye(280)}=A_{478}\times(A_{280}/A_{478})$standard. The concentration of protein was then $C_{prot(280)}=280/A_{prot(280)}$. Table 1 summarizes the change in fluorescence of various GGBP mutants labeled with reporter groups, including reporting groups having either excitation or emission maximum of at least 600 nanometers. Table 2 summarizes the change in fluorescence, and determined Kd values of mutations of one, two, three, and four amino acid substitutions. This data clearly shows mutations of GGBP labeled with reporter group can provide desirable attributes as glucose biosensors. The data shows the mutation-reporter group relationship for the samples tested. FIG. 1 illustrates the change in fluorescence response to various glucose concentrations of A213C/L238C NBD amide GGBP $H_6$, as a representative example, in solution. FIG. 2 illustrates the change in fluorescence response to various glucose concentrations of E149C/A213R NBD amide GGBP $H_6$, as yet another representative example, in solution.

TABLE 1

Percent Change in Fluorescence for GGBP Mutants[1]

| Dye | Excitation/ emission (nm) | S112C | M182C | A213C | A213C $His_6$ | M216C |
|---|---|---|---|---|---|---|
| IANBD amide | 470/550 | 0 | 4 | 3 | 51 | 7 |
| IANBD ester | 470/550 | | | | | |
| IAEDANS | 336/490 | −7 | −8 | 0 | | −9 |
| Bodipys530/550IA | 530/550 | 7 | −10 | 33 | | 4 |
| XRIA 5, 6 | 575/600 | −21 | −19 | −38 | | −15 |
| Lucifer Yellow IA | 426/530 | | | −14 | | −3 |
| Bodipy 507/545 IA | 507/545 | | | 25 | | −3 |
| Cy5 | 640/660 | 2 | 0 | 11 | | −7 |
| Texas Red-maleimide | 580/610 | | | | −13 | |
| Dapoxyl | 375/580 | 15 | 7 | 12 | | 2 |

[1]F from 0 to 1 mM glucose at 0.5 uM [dye]. Unless otherwise indicated all mutants were w/o histidine tags.

This example describes the detectable signal change evident upon glucose binding to the mutated GGBP labeled with luminescent labels and the determination of Kd.

The change in fluorescence (ΔF, Table 2) was measured as the percent difference in fluorescence between 0 and 1 mM glucose at 0.5 μM protein using an SLM Aminco fluorimeter (Ontario, Canada) with slit settings of 8 and 4 for excitation and settings of 5 and 5 on the MC250 emission monochromator.

Binding constants (Table 2) were determined by titration of increasing concentrations of glucose into a 0.1 μM protein solution (PBS, 013 mM NaCl) with mixing following each addition of glucose. Slit settings were the same as listed above. The Kd was determined from the following relationships as adapted from Pisarchick and Thompson (1990):

$$F = \frac{F_{inf} + F_0 - F_{inf}}{1 + x/Kd} \quad (1)$$

where F is fluorescence intensity, $F_{inf}$ is fluorescence at infinity, $F_0$ is fluorescence at zero glucose, and x is the free concentration of glucose ($[Glc]_{free}$) as determined by the relationship:

$$[GLc]_{free} = \frac{[GLC]_{tot} - [Prot]_{tot} - Kd + \sqrt{([Glc]_{tot} - [Prot]_{tot} - Kd)2 + 4*[Glc]_{tot}*Kd}}{2}$$

where $[Glc]_{tot}$ and $[Prot]_{tot}$ are the total concentrations of glucose and protein, respectively.

TABLE 2

Summary of GGBP-H6 NBD Mutations

| Identification | ΔF (%)[1] | Solution Kd (mM)[2] | Dye/Pot | Seqncd |
|---|---|---|---|---|
| wild type | intrinsic | 0.0002 | — | for/rev |
| A1C | — | | | |
| K11C | 10 | — | 1.8 | rev |
| D14C | 1 | — | 1.5 | rev |
| V19C | −56 | 0.0001 | 0.38 | |
| N43C | 40 | 0.0002 | 0.28 | |
| G74C | −3 | 0.0009 | 1.43 | — |
| Y107C | −30 | 0.001 | 0.93 | for |
| T110C | −9 | — | | for/rev |
| S112C | 220 | 0.05 | 1.15 | — |
| S112C, L238S | 6 | — | 1.5 | — |
| K113C | 15 | — | 0.65 | — |
| K137C | −5 | 0.00004 | 1.17 | — |
| E149C | 300 | 0.0002 | 0.96 | — |
| E149C, A213R | 660 | 1 | 1.1 | for/rev |
| E149C, K223N | — | — | — | — |
| E149C, L238S | 660[4] | 0.08 | 1.36 | for/rev |
| E149C, N256S | 1 | — | 0.93 | for/rev |
| E149C, M182C, A213C, L238S | 200 | 216[6] | 3.2 | for/rev |
| E149C, A213S, L238S | 480 | 0.47 | 0.76 | for/rev |
| E149C, A213R, L238S | 500 | 35 | — | — |
| H152C, A213R | −3 | — | 1.2 | for/rev |
| H152C, A213S | 100 | 0.16 | — | — |
| H152C, K223N | 200 | 0.003 | 1 | for |
| M182C | 11 | — | — | for/rev |
| A213C | 50 | 0.124 | 0.68 | for/rev |
| A213C, L238C | 24, 67[3] | 6 | 1.4 | for/rev |
| M216C | 67 | 0.008 | 0.91 | for |
| L238C | −6, +3[3] | — | 1.3 | for/rev |
| D287C | 4 | — | 1.1 | for |
| R292C | −34 | 0.0008 | 1.5 | for |

Figure 3:
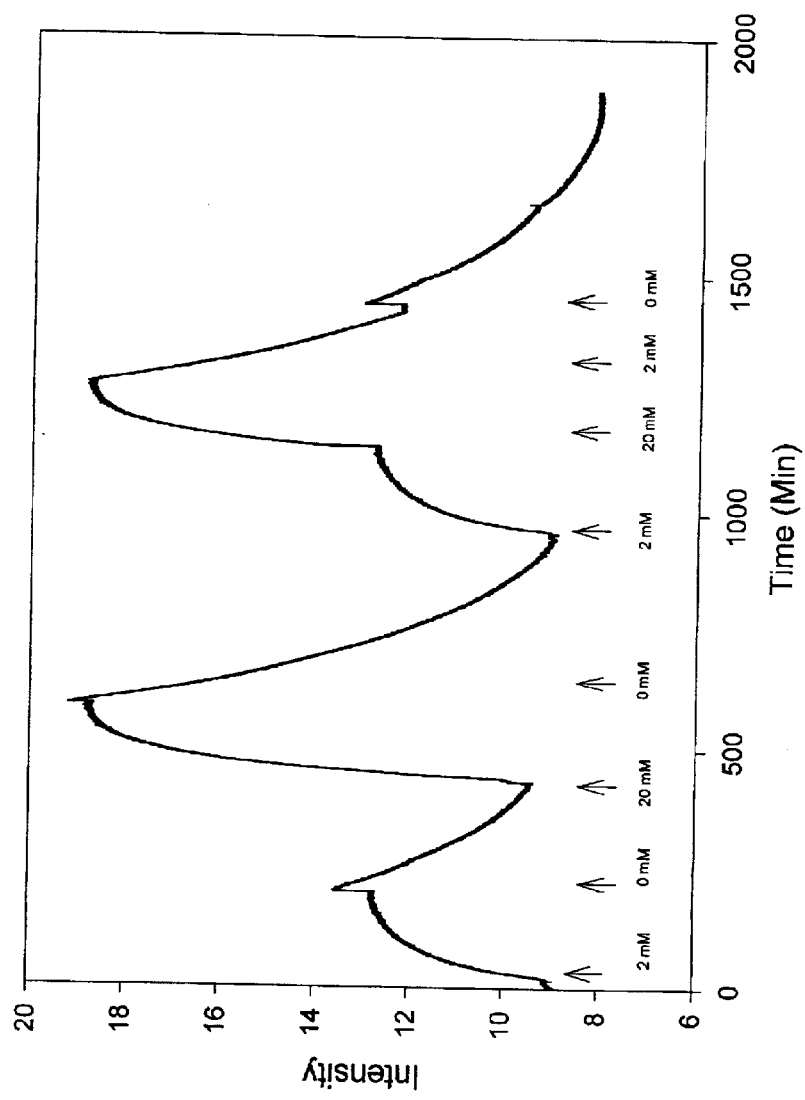
FIG. 3 illustrates reversible signal transduction from a mutated binding protein.

[1] ΔF from 0 to 1 mM Glc at 0.5 μM [NBD]
[2] Kd measured at 0.1 μM [dye]
[3] ΔF when measured from 0 to 100 mM Glc
[4] ΔF when measured from 0 to 10 mM Glc
[5] Estimated; Sigma Plot calc. did not converge
[6] Estimated; curve did not reach saturation
Seqncd = sequencing, for = forward; rev = reversed; for/rev = both This example describes the immobilization of a biosensor of the instant invention into a dialysis membrane matrix and the ability of the matrix to provide reversible and continuous readings. Using a Varian Eclipse fluorimeter with a fiber optic attachment, GGBP L238C/A213C protein (2 M in PBS buffer) entrapped within a dialysis membrane having a molecular cut-off of 3500 Daltons affixed to the distal end of the fiber. Solutions were prepared containing PBS buffer, 2 mM, and 20 mM glucose in PBS buffer. With the probe in PBS solution, readings were recorded at 0.02 seconds intervals of the emmision wavelength 521 nm, followed by insertion of the fiber into the glucose solutions. Replacement of the fiber into buffer-only solution resulted in the return of initial signal. FIG. 3 depicts multiple cycles alternating between buffer and glucose solutions demonstrating the reversibility of the biosensor entrapped within a permeable matrix within physiological range.

We claim:

1. A glucose biosensor comprising at least one mutated glucose/galactose binding protein and at least one reporter group attached to said binding protein, such that said reporter group provides a detectable and reversible signal change when said mutated binding protein is exposed to varying glucose concentrations;
   wherein said at least one mutated glucose/galactose binding protein comprises at least one amino acid substitution selected from the group consisting of a cysteine at position 11, a cysteine at position 14, a cysteine at position 19, a cysteine at position 43, a cysteine at position 74, a cysteine at position 107, a cysteine at position 110, a cysteine at position 112, a cysteine at position 113, a cysteine at position 137, a cysteine at position 149, a cysteine at position 213, a cysteine at position 216, a cysteine at position 238, a cysteine at position 287, and a cysteine at position 292, and
   wherein said detectable and reversible signal change is related to said varying concentrations.

2. The biosensor of claim 1 wherein said reporter group is a luminescent label.

3. The biosensor of claim 1, wherein said mutated glucose/galactose binding protein has at least one histidine tag.

4. The biosensor of claim 2 wherein said luminescent label is covalently coupled to said at least one mutated glucose/galactose binding protein.

5. The biosensor of claim 4 wherein said luminescent label has an excitation wavelength of more than about 600 nanometers.

6. The biosensor of claim 4 wherein said luminescent label has an emission wavelength of more than about 600 nanometers.

7. The biosensor of claim 4, wherein said luminescent label is selected from the group consisting of fluorescein, coumarins, rhodamines, 5-TMRIA (tetramethylrhodamine- 5-iodoacetamide), (9-(2(or 4)-(N-(2-maleimdylethyl)-sulfonamidyl)-4(or 2)-sulfophenyl)-2,3,6,7,12,13,16,17-octahydro-(1H,5H,11H,15-xantheno(2,3,4-ij:5,6,7-i'j') diquinolizin-18-ium salt), 2-(5-(1-(6-(N-(2-maleimdylethyl)-amino)-6-oxohexyl)-1,3-dihydro-3,3-dimethyl-5-sulfo-2H-indol-2-ylidene )-1,3-propyldienyl)-1-ethyl-3,3-dimethyl-5-sulfo-3H-indolium salt, N-((2-iodoacetoxy)ethyl)-N-methyl)am-ino-7-nitrobenzoxadiazole, 6-acryloyl-2-dimethylaminonaphthalene, pyrene, 6-amino-2,3-dihydro-2-(2-((iodoacetyl)amino)ethyl)-1,3-dioxo-1H-benz(de)isoquinoline-5,8-disulfonic acid salt, 2-(5-(1-(6-N-(2-maleimdylethyl)-amino)-6-oxohexyl)-1,3-dihydro-3,3-dimethyl-5-sulfo-2H-indol-2ylidene)-1,3-pentadienyl)-1-ethyl-3,3-dimethyl-5-sulfo-3H-indolium salt, 4-(5-(4-dimethylaminophenyl)oxazole-2-yl)-N-(2-bromoacetamidoethyl)sulfonamide, (N-(4,4-difluoro-1,3,5,7-tetramethyl-4-bora-3a,4a-diaza-s-indacene-2-yl)iodoacetamide, N-(4,4-difluoro-5,7-diphenyl-4-bora-3a,4a-diaza-s-indacene-3-propionyl)-N-'-iodoacetylethylenediarnine, 5-((((2-iodoacetyl)amino)ethyl)amino)naphthalene-1-sulfonic acid, and carboxy-X-rhodamine, 5/6-iodoacetamide.

8. A glucose biosensor comprising at least one mutated glucose/galactose binding protein and at least one reporter group attached to said binding protein, such that said reporter group provides a detectable and reversible signal change when said mutated binding protein is exposed to varying glucose concentrations;

wherein said at least one mutated glucose/galactose binding protein comprises at least two amino acid substitutions, said at least two amino acid substitutions being selected from the group consisting of a cysteine at position 112 and a serine at position 238, a cysteine at position 149 and a serine at position 238, a cysteine at position 152 and a cysteine at position 182, a cysteine at position 152 and a serine at position 213, a cysteine at position 213 and a cysteine at position 238, a cysteine at position 149 and an arginine at position 213; and wherein said detectable and reversible signal change is related to said varying concentrations.

9. The biosensor of claim 8 wherein said reporter group is a luminescent label.

10. The biosensor of claim 8, wherein said mutated glucose/galactose binding protein has at least one histidine tag.

11. The biosensor of claim 9 wherein said luminescent label is covalently coupled to said at least one mutated glucose/galactose binding protein.

12. The biosensor of claim 11 wherein said luminescent label has an excitation wavelength of more than about 600 nanometers.

13. The biosensor of claim 11 wherein said luminescent label has an emission wavelength of more than about 600 nanometers.

14. The biosensor of claim 11, wherein said luminescent label is selected from the group consisting of fluorescein, coumarins, rhodamines, 5-TMRIA (tetramethylrhodamine-5-iodoacetamide), (9-(2(or 4)-(N-(2-maleimdylethyl)-sulfonamidyl)-4(or 2)-sulfophenyl)-2,3,6,7,12,13,16,17-octahydro-(1H,5H,11H,15H-xantheno(2,3,4-ij:5,6,7-i'j') diquinolizin-18-ium salt), 2-(5-(1-(6-(N-(2-maleimdylethyl)-amino)-6-oxohexyl)-1,3-dihydro-3,3-dimethyl-5-sulfo-2H-indol-2-ylidene )-1,3-propyldienyl)-1-ethyl-3,3-dimethyl-5-sulfo-3H-indolium salt, N-((2-iodoacetoxy)ethyl)-N-methyl)am-ino-7-nitrobenzoxadiazole, 6-acryloyl-2-dimethylaminonaphthalene, pyrene, 6-amino-2,3-dihydro-2-(2-((iodoacetyl)amino)ethyl)-1,3-dioxo-1H-benz(de)isoquinoline-5,8-disulfonic acid salt, 2-(5-(1-(6-N-(2-maleimdylethyl)-amino)-6-oxohexyl)-1,3-dihydro-3,3-dimethyl-5-sulfo-2H-indol-2-ylidene)-1,3-pentadienyl)-1-ethyl-3,3-dimethyl-5-sulfo-3H-indolium salt, 4-(5-(4dimethylaminophenyl)oxazole-2-yl)-N-(2-bromoacetamidoethyl)sulfonamide, (N-(4,4-difluoro-1,3,5,7-tetramethyl-4-bora-3a,4a-diaza-s-indacene-2-yl)iodoacetamide, N-(4,4-difluoro-5,7-diphenyl-4-bora-3a,4a-diaza-s-indacene-3-propionyl)-N-'-iodoacetylethylenediamine, 5-((((2-iodoacetyl)amino)ethyl)amino)naphthalene-1-sulfonic acid, and carboxy-X-rhodamine, 5/6-iodoacetamide.

15. A glucose biosensor comprising at least one mutated glucose/galactose binding protein and at least one reporter group attached to said binding protein, such that said reporter group provides a detectable and reversible signal change when said mutated binding protein is exposed to varying glucose concentrations;

wherein said at least one mutated glucose/galactose binding protein comprises at least three amino acid substitutions, said at least three amino acid substitutions being selected from the group consisting of a cysteine at position 149 and a serine at position 213 and a serine at position 238, and a cysteine at position 149 and an arginine at position 213 and a serine at position 238; and wherein said detectable and reversible signal change is related to said varying concentrations.

16. The biosensor of claim 15 wherein said reporter group is a luminescent label.

17. The biosensor of claim 15 wherein said mutated glucose/galactose binding protein has at least one histidine tag.

18. The biosensor of claim 16 wherein said luminescent label is covalently coupled to said at least one mutated glucose/galactose binding protein.

19. The biosensor of claim 18 wherein said luminescent label has an excitation wavelength of more than about 600 nanometers.

20. The biosensor of claim 18 wherein said luminescent label has an emission wavelength of more than about 600 nanometers.

21. The biosensor of claim 18, wherein said luminescent label is selected from the group consisting of fluorescein, coumarins, rhodamines, 5-TMRIA (tetramethylrhodamine-5-iodoacetamide), (9-(2(or 4)-(N-(2-maleimdylethyl)-sulfonamidyl)-4(or 2)-sulfophenyl)-2,3,6,7,12,13,16,17-octahydro-(1H,5H,11H,15H-xantheno(2,3,4-ij:5,6,7-i'j') diquinolizin-18-ium salt), 2-(5-(1-(6-(N-(2-maleimdylethyl)-amino)-6-oxohexyl)-1,3-dihydro-3,3-dimethyl-5-sulfo-2H-indol-2-ylidene)-1,3-propyldienyl)-1-ethyl-3,3-dimethyl-5-sulfo-3H-indolium salt, N-((2-iodoacetoxy)ethyl)-N-methyl)am-ino-7-nitrobenzoxadiazole, 6-acryloyl-2-dimethylaminonaphthalene, pyrene, 6-amino-2,3-dihydro-2-(2-((iodoacetyl)amino)ethyl)-1,3-dioxo-1H-benz(de)isoquinoline-5,8-disulfonic acid salt, 2-(5-(1-(6-N-(2-maleimdylethyl)-amino)-6-oxohexyl)-1,3-dihydro-3,3-dimethyl-5-sulfo-2H-indol-2-ylidene)-1,3-pentadienyl)-1-ethyl-3,3-dimethyl-5-sulfo-3H-indolium salt, 4-(5-(4-dimethylaminophenyl)oxazole-2-yl)-N-(2-bromoacetamidoethyl)sulfonamide, (N-(4,4-difluoro-1,3,5,7-tetramethyl-4-bora-3a,4a-diaza-s-indacene-2-yl)iodoacetamide N-(4,4-difluoro-1,3,5,7-diphenyl-4-bora-3a,4a -diaza-s-indacene-3-propionyl)-N-'-iodoacetylethylenediamine, 5-((((2-iodoacetyl)amino)ethyl)amino)naphthalene 1-sulfonic acid, and carboxy-X-rhodamine, 5/6-iodoacetamide.

* * * * *